United States Patent [19]

Prier

[11] Patent Number: 4,834,802
[45] Date of Patent: May 30, 1989

[54] HEAT GENERATING TOURNIQUET FOR VENIPUNCTURE APPLICATIONS

[76] Inventor: David A. Prier, 3008 Salluce Dr., Denair, Calif. 95316

[21] Appl. No.: 82,305

[22] Filed: Aug. 6, 1987

[51] Int. Cl.$^4$ ............................................. A61B 17/12
[52] U.S. Cl. ................................. 128/327; 128/402; 604/291
[58] Field of Search ............... 128/327, 325, 26, 113, 128/115, 402, 1 R; 604/2, 289, 290, 291; 206/219, 222; 126/263

[56] References Cited

U.S. PATENT DOCUMENTS

| | | | |
|---|---|---|---|
| 1,824,516 | 9/1931 | Tyuand | 128/327 |
| 2,157,169 | 9/1937 | Foster | 206/222 |
| 2,234,961 | 3/1941 | Canada | 128/327 |
| 3,463,161 | 8/1969 | Andrassy | 128/402 |
| 3,620,209 | 11/1971 | Kravitz | 128/41 |
| 3,951,127 | 4/1976 | Watson | 126/206 |
| 3,998,210 | 12/1976 | Nosari | 128/736 |
| 4,057,047 | 11/1977 | Gossett | 206/219 |
| 4,067,313 | 1/1978 | Donnelly | 206/219 |
| 4,314,568 | 2/1982 | Loving | 128/327 |
| 4,316,461 | 2/1982 | Marais | 128/214 |
| 4,516,564 | 5/1985 | Koiso et al. | 126/263 |
| 4,573,447 | 3/1986 | Thrash | 126/263 |
| 4,586,924 | 5/1986 | Lanning | 604/115 |

*Primary Examiner*—John D. Yasko
*Attorney, Agent, or Firm*—Stetina and Brunda

[57] ABSTRACT

A disposable tourniquet having a plastic strap and a windowed plastic pad defining a pair of liquid storage reservoirs mutually separated by a frangible wall. Bending of the pad breaks the frangible wall, comingling liquid solutions of water and hydrochloric acid and causing exothermic reaction heating on the order of 105-107 degrees F. When the pad is forcibly secured by the strap in contact with a patient's skin and with a portion of the patient's blood vessel lying within the window of the pad, then the skin is mechanically puffed up through the window and the blood vessel is mechanically stabilized. The blood vessel is simultaneously locally vasodilated. After venipuncture of the dilated vein through the window, the pad body is severable by a ripcord for quick removal from the venipuncture site.

29 Claims, 1 Drawing Sheet

HEAT GENERATING TOURNIQUET FOR VENIPUNCTURE APPLICATIONS

BACKGROUND OF THE INVENTION

1. Field of the Invention

The present invention concerns medical tourniquet devices for stabilizing and/or for inducing vasodilation of human veins in support of the venipuncture of or intravenous insertions into such veins.

2. Description of the Relevant Art

When in medical therapy or diagnosis it becomes necessary to puncture a human's blood vessel, nominally a vein, with a needle or syringe in order to inject medication, remove blood and/or make an intravenous connection, it is necessary to (i) locate a suitable vein and subsequently (ii) insert a needle through the skin (i.e. soft tissue) and into the interior of the vein. Sometimes during this procedure a suitable vein proves difficult to locate as well as often difficult to reliably insert the needle into its interior. Difficulties in location and/or insertion may exist because the walls of the patient's vein have degenerated at the site of venipuncture either from the effects of previous punctures because the patient is elderly or obese, and/or because the patient's vein is prone to roll from side to side. When a venipuncture is not reliably performed upon an initial attempt then it causes, at the minimum, additional discomfort and accumulative injury to the patient when the venipuncture is repeated. Unreliably performed venipuncture can also magnify and compound damage to the veins. Finally, unreliably performed venipuncture potentially results in poor intravenous connection for the collection of blood and/or the administration of therapeutic agents.

Devices for holding, stabilizing, constricting, immobilizing, and/or stimulating veins during medical venipuncture in order to aid the successful performance thereof are known in the prior art. U.S. Pat. No. 2,234,961 for a VEIN HOLDER to P. L. Canada shows a tourniquet in combination with a device for holding an adjacent vein against movement in order to facilitate intravenous injections and the like. The holding device comprises an arm of complex structure including a pressure member with fingers spaced to receive between them the vein which is to be punctured. Canada generally shows that a vein may be mechanically held not only against movement, but may also be held in high relief to aid medical personel in performing venipuncture.

U.S. Pat. No. 4,314,568 for VASCULAR STABILIZER to Loving shows an adjustable and disposable device maintained on a human appendage, and in pressured contact with the flesh about the location of a vein, by a strap. A living hinge portion connects two half body portions and permits a pivotal motion whereby ribs on each half-bodied portion may be brought together in parallel in order to stabilize a blood vessel lined between the ribs. A step locking mechanism prevents pivotal motion in a retrograde direction and thus ensures that the device is used for only a single venipuncture procedure, thereby preventing cross-contamination between patients. Loving generally shows that mechanical force may be used against the skin of a patient in order to draw a vein nearer to the surface of the skin.

U.S. Pat. No. 4,586,924 for VEIN CONSTRICTOR AND IMMOBILIZER for Lanning shows a device having a pressure plate which is hand held in pressured contact with the skin at the position of a vein. The planar pressure plate has in one of its ends a notch entirely through its thickness. At the apex of the notch a tapered groove is present within the bottom surface of the pressure plate. This tapered groove starts at the apex of the notch and terminates at the bottom surface of the pressure plate at a position intermediate the apex and the opposing edge of the pressure plate. When the groove and notch are both placed in pressured contact about the vein, they combinatorially constrict and immobilize the vein so as to allow venipuncture at the position of the notch. Lanning generally shows that veins may be mechanically constricted longitudinally, as well as laterally, along their length.

U.S. Pat. No. 4,316,461 for INTERVENOUS VASULAR STABILIZER to Marais, et al. discloses a method of performing venipuncture through a cutaway section within a central slot of a base plate, which slot overlays a vein. The slot is defined by an arched connector, or hood portion, which rigifies the slot and protects a needle-type catheder in its inserted positon. By exerting pressure on this connector, or hood, portion then the base is pressed downwardly on either side of the vein, which vein is then noticeably elevated into the slot area as well as being laterally stabilized. The pressure plate is held in position upon the human flesh and about the vein by straps. Marais, et al. generally shows that lateral pressure about a vein is useful for its mechanical stabilization during venipuncture.

Soft tissue in the area of veins may be mechanically manipulated other than in direct support of venipuncture. An example of the prior art showing mechanical manipulation of a vein at the site of venipuncture is contained within U.S. Pat. No. 3,620,209 for DEVICE FOR REDUCING THE PAIN OF INJECTIONS OF MEDICINES AND OTHER BILOGICALS to Kravitz. This patent shows a device which is held upon the skin, nominally by straps, and which vibrates the skin about the injection area. The vibration stimulates the pain center of the skin so that the pain of injections perceived by the patient may be minimized. Generally Kravitz indicates that stimuli, particularly taught to be mechanical stimuli, which is applied to the skin at or near the site of injection is potentially beneficial in mitigating or alleviating the patient's perception of pain associated with injection.

Also of relevance to the present invention is certain prior art concerned with the application of heated medical compresses to the skin, and the manner of generating heat externally or internally to such heated compresses. In this regard, U.S. Pat. No. 3,951,127 for CONSTANT TEMPERATURE DEVICE to Watson, et al., discloses a chemical heating device useable in medical applications. Specifically, a flexible container of a substantially planar configuration encloses a reservoir within which a first and second chemical may be combined in order to produce constant temperature heating. The resulting heated device is effected for use as a warm baby mattress, a warm blanket, or a hot water bottle substitute.

U.S. Pat. No. 3,463,161 for TEMPERATURE MAINTAINING DEVICE to Andrassy shows a flexible container containing a composition which is permanently plastic at temperatures throughout the range of zero degrees to one hundred and fifty degrees F. The container as well as its composition remains relatively soft and plastic during use. The container is generally divided into compartments by barriers and/or dividers. Andrassy generally shows that flexible containers which are useful in medical applications and which contain emulsions or dispersions may be readily fabricated.

U.S. Pat. No. 4,573,447 for CHEMICAL HEATER to Thrash, et al., discloses a chemical heater having a ruptureable container inside a substantially puncture- and rupture-proof envelope. After rupture of the inner container, heat is produced by exothermic reation. The particular chemical compositions, and the particular concentrations of chemicals within these compositions, which allow attainment of some desired exothermic reaction temperature are described.

SUMMARY OF THE INVENTION

The present invention is embodied in a disposable heat-generating tourniquet, and a method of using such a tourniquet in support of venipuncture or the making of intraveneous connections. The purpose of the tourniquet, and the method of its use, is to both (i) stabilize and (ii) vasodilate a vein which is subject to venipuncture. The stabilization is by mechanical means. The vein is stabilized by physically locking, or immobilizing, it within a window of a tourniquet pad portion of the device. The simultaneous vasodilation is both by mechanical means and also by thermal means. The vein is vasodilated, causing the vein to pressurize and swell, by subjecting it to (i) selective constriction and (ii) the application of heat by the same tourniquet pad portion in an area adjacent to the vein.

In one of its aspects, the disposible tourniquet in accordance with the present invention includes a pad portion which defines a substantially central window aperture. This pad portion, when pressured by a tourniquet strap portion against a patient's skin in a position about a vein, physically immobilizes and stabilizes this vein. Venipuncture may then be accomplished on that portion of the vein which is outlined within the tourniquet's window aperture without any attendant rolling or movement of the vein. This window aperture aspect of the present invention is, without more, efficacious in support of venipuncture.

In another of its aspects, the disposable tourniquet in accordance with the preent invention has a pad portion which is not of equal thickness. The pad portion of the tourniquet has a contour which initially increases in thickness radially from its window aperture. The tourniquet pad portion is also pliable and resilient, particularly because the pad portion preferably defines and contains one or more fluid reservoirs. The aperture window, the contours, and the flexible compliance of the pad portion are, without more, sufficient to cause the patient's skin and a portion of his vein to "puff up" through the window aperture. This puffing further facilitates locating, immobilizing, and stabilizing the vein for the purpose of venipuncture.

In still another of its aspects, the tourniquet in accordance with the present invention thermally induces vasodilation of the vein which it also immobilizes. Specifically, the pad portion of the tourniquet preferably defines a pair of storage reservoirs, preferably one reservoir within another. The reservoirs contain chemicals, preferably, but not necessarily limited to liquids, which are capable of producing an exothermic reaction upon mixing. A barrier which is located between the reservoirs, or which constitutes the wall of the inner reservoirs, is frangible and may be manually ruptured, allowing he chemicals to mix. This mixing initiates an exothermic reaction of a temperature sufficient to induce vasodilation of that vein in the region about which the pad portion of the tourniquet is temporarily affixed, yet insufficient to cause damage, i.e. burn the soft tissue of the patient. This vasodilation swells and distends the vein, allowing it to further engorge with blood thereby enhancing venipuncture.

The tourniquet in accordance with the present invention further preferably includes a reusable tape tab for easy affixation to the limb of a patient. A frangible path, lined by a ripcord, is preferably provided between the window aperture and outer the periphery of the pad portion. Upon those instances that a butterfly intravenous needle, or other medical instrument is left inserted within a vein, then the tourniquet may readily be removed from about the medical instrument by fracturing, or ripping, along this predetermined frangible path. The tourniquet is preferably entirely disposable after use.

BRIEF DESCRIPTION OF THE DRAWINGS

These and other aspects of the present invention will become increasing clear upon reference to the drawings wherein.

DESCRIPTION OF THE PREFERRED EMBODIMENT

The present invention is concerned with stabilizing, immobilizing, controlling blood flow through, physically squeezing into a "puffed up" position of prominence relative to the surrounding skin, and vasodilating human blood vessels all in support of the medical puncture of such vessels. Particularly, the present invention is concerned with (i) mechanically (including hydrodynamically) and (ii) thermally manipulating human veins is support of venipuncture, or the intravenous entrance of medical syringes and needles into such veins.

Figure 1:
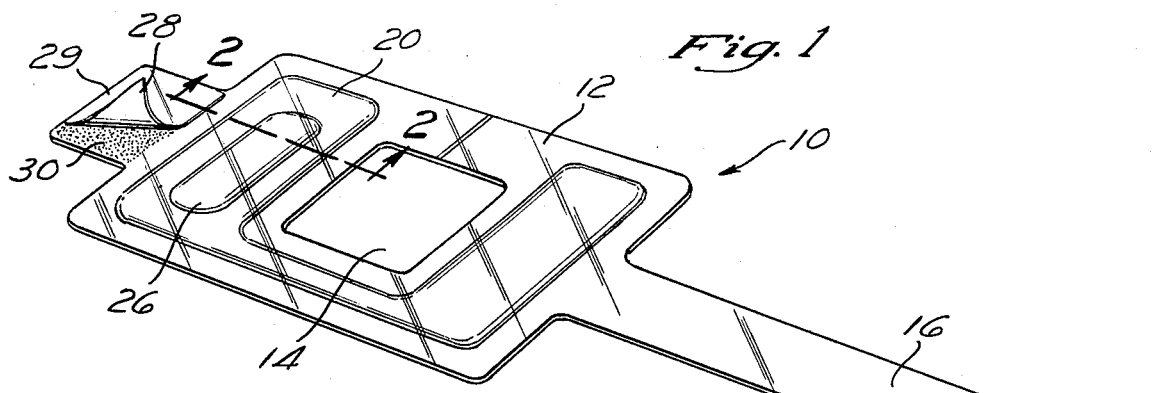
FIG. 1 is a perspective view showing the preferred embodiment heat generating tourniquet for venipuncture applications in accordance with the present invention.

The present invention is embodied in a heat generating tourniquet, and the method for the use of such tourniquet. A preferred embodiment tourniquet in accordance with the present invention is generally shown in drawings FIGS. 1-5. Within drawing FIG. 1 the tourniquet 10 may be seen to generally include an elongate strap portion 16 which is preferably fabricated of a plastic material formed integrally with a pad portion 12 and tab portion 29. The integral tab portion or area 29 is preferably covered with an adhesive 30 which is applied to the tourniquet surface and covered by a removable plastic cover or slip sheet 28.

Figure 4:
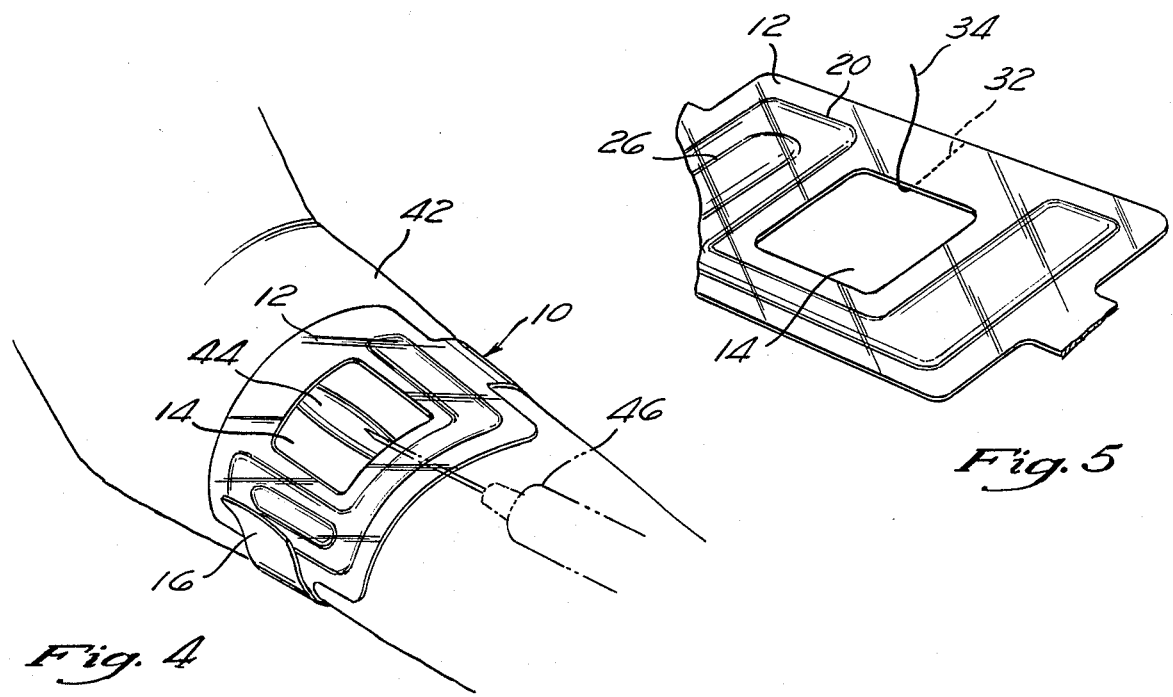
FIG. 4 is a diagrammatic representation showing the manner of accomplishing venipuncture through the window aperture within the preferred embodiment tourniquet in accordance with the present invention.

As illustrated in FIG. 4, the tourniquet 10 may readily be mounted upon a human appendage, illustrated by example to be arm 42. Tourniquet 10 is mounted by removing the cover sheet 28 from the pad area 29, wrapping the strap portion 16 tightly around the human appendage, and then pressing the strap portion 16 tightly into contact with adhesive 30 at an appropriate extension along such strap portion 16. The strap portion 16 is formed sufficiently long to encircle desired appendage, and may be trimmed to length with scissors as desired either before or after mounting. If the unused length of the strap portion 16 is not trimmed then it flops harmlessly, and does not interfere with venipuncture.

Returning to FIG. 1, the pad portion 12 of tourniquet 10 defines a substantially central window aperture 14. This window aperture 14 may be of various shapes, but is preferably a rectangle which is centrally and symetrically located within pad portion 12. Again referring to FIG. 4, two opposed edges of the window aperture 14 to pad portion 12 will normally lie transversely across a human blood vessel (which generally runs longitudinally along a human appendage) when the window aperture 14 is positioned about such a blood vessel during operational use of tourniquet 10. In accordance with the general constriction principle of a tourniquet, the tourniquet 10 will stop blood flow within the blood vessel or vein, illustrated by example in FIG. 4 to be a vein 44. With the tourniquet 10 in place, the pad portion 12 of the tourniquet 10 may optionally be momentarily lifted with the finger at the portion of pad 12 which is upstream to vein 44, which vein 44 the pad 12 otherwise partially encloses within window aperture 14. This optional, momentary, lifting allows blood to accumulate within the apertured portion of vein 44 under the hydrodynamic pressure of the body's normal circulatory system. A slight distension, or swelling, or vasodilation of the vein 44 within the region of window aperture 14 may thus be immediately obtained. The finger may be used to enhance this effect by poking, prodding, and massaging flesh and blood toward the window aperture 14.

Therefore, as one aspect with in accordance with the present invention, a tourniquet defines a window aperture within which a human blood vessel may be positioned. Medical puncture of the blood vessel may transpire while the blood vessel is stabilized within this aperture window. In this regard, the vein is stabilized within the window by opposite end portions of the pad portion 12 clamping or anchoring down opposite ends of the vein therebenath, thereby eliminating any rolling of the vein within the vicinity of the window aperture 14. Furthermore, this particular apertured geometry presents an immediate opportunity to manipulate the edge of the tourniquet pad and the underlying flesh at the region of the window aperture in order to both mechanically and hydrodynamically cause a portion of a blood vessel within the window aperture became prominent by being both "puffed up" and mechanically (hydrodynamically) vasodilated.

Figure 2:
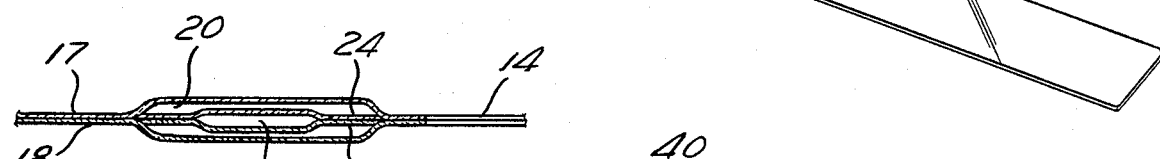
FIG. 2 is a cross-sectional view, taken along aspect line 2—2 shown in FIG. 1, of the preferred embodiment tourniquet in accordance with the present invention.

Still another aspect of the present invention concerns thermal vasodilation of the blood vessel otherwise held in position by the tourniquet. Returning to FIG. 2, it may be noted that pad portion 12 is formed by a pair of layers 17, 18 which define a first cavity or reservoir 20. This reservoir 20 preferably extends around the substantial portion of pad portion 12. An additional reservoir is located within pad portion 12. This reservoir may be at an independent location within pad 12 where it is separated from the first reservoir 20 by a frangible wall, or may preferably be, as illustrated in FIG. 2, a second reservoir 26 which is entirely contained within the first reservoir 20. This reservoir 26 is defined by and held in position by sheets or walls 22, 24.

Figure 3:
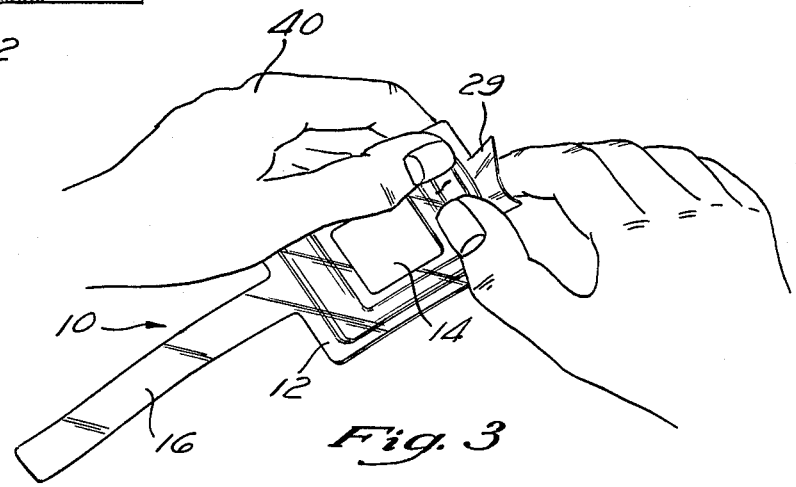
FIG. 3 is a diagrammatic representation of the manner of actuating the exothermic reaction within the preferred embodiment tourniquet in accordance with the present invention.

In accordance with the present invention, the first reservoir 20 and the second reservoir 26 each independently and separately store a chemical, preferably a fluid, which is capable of producing an exothermic chemical reaction upon mixing with the chemical of the other reservoir. The boundary between reservoirs is frangible, and subject to being ruptured by hand manipulation. Particularly in the preferred embodiment, the walls of second reservoir 26 located entirely within first reservoir 20 may be ruptured by twisting or squeezing with the human hand 40 as illustrated in FIG. 3. The resulting mixing or commingling of the seperate chemicals previously stored within first reservoir 20 and second reservoir 26 results within an exothermic chemical reaction. This exothermic reaction preferably produces temperatures in the range of 105 degrees F. to 107 degrees F. A number of chemicals, both dry and liquid, which permit the generation of a safe exothermic reaction in this particular temperature range are taught within those patents identified within the Background of the Invention section to this specification disclosure. The teachings of those patents regarding the generation of medically theraputic exothermic chemical reactions are incorporated herein by reference. A preferred exothermic reaction will produce and sustain a temperature in the indicated range for a time period in excess of three minutes, which allows adequate time for deployment and use of the tourniquet in accordance with the present invention.

When the tourniquet 10 in accordance with the present invention produces heat by a commingling of chemicals in order to produce an exothermic reaction, then the tourniquet 10 will be warm when applied to the human arm 42 in a position about the blood vessel 44. The heat provided by the tourniquet 10 will cause vasodilation of the blood vessel 44, including both dimensional and coloration changes which still further serve to make the blood vessel 44 prominent within the region of window aperture 14.

Therefore, in accordance with the present invention the blood vessel 44 is simultaneously stabilized, distended by internal hydrodynamic pressure, "puffed-up" above the surface of the surrounding skin and vasodilated, meaning widened or distended. Particularly by the synergistic combination of all this mechanical and thermal manipulation, the blood vessel 44, even if its walls are corroded and damaged, will be presented to needle or syringe 46 as best as is possible. So presented, the blood vessel 44 is more probable of being successfully medically punctured than would otherwise be the case.

Figure 5:
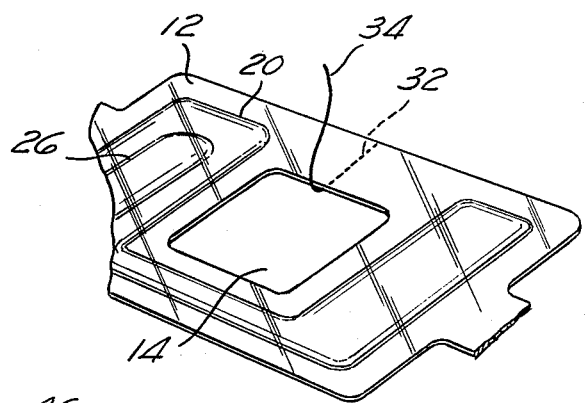
FIG. 5 is a partial perspective view of the preferred embodiment tourniquet in accordance with the present invention particularly showing the ripcord by which a channel may be opened within the pad portion of the tourniquet from the pad edge to the window aperture.

In the event of venipuncture by a syringe for the withdrawal of blood from a vein, or upon the occasion of the injection of any blood vessel, then after a withdrawal of the needle, or syring, 46 the tourniquet 10 is left disposed upon the arm 42. The strap 16 may be peeled from contact with adhesive 30 on tab 29 and the entire tourniquet 10 may be summarily discarded. However, in those instances that a continuing, semi-permanent, intravenous connection to blood vessel 44 is desired, the present invention provides a means to enable removal of the tourniquet from the patient without disturbing the existing intervenous connection. This means is illustrated in FIG. 5 and comprises means for severing a portion of the pad portion 12 to enable the same to be manually spread and removed from the patient. This severance is facilitated by a frangible channel, fracturable joint, or severable line or the like formed in the pad portion 12. Particularly in accordance with the preferred embodiment tourniquet 10 of the present invention which is illustrated in FIG. 5, it is preferred that the body portion 12 should be capable of being ripped and severed along a channel or demarcation line 32. The severance of body portion 12 long this line is facilitated by rip cord 34. When the window aperture 14 to body portion 12 is so opened by pulling the rip cord, then the tourniquet 10 may readily be removed from its position about any medical apparatus which remains in position within blood vessel 44 (shown in FIG. 4).

The heat-generating tourniquet in accordance with the present invention has been seen to exhibit diverse mechanical and thermal aspects. Many of these aspects are separate and severable, and could readily be recombined to produce alternative tourniquet structures by a practitioner in the design of medical appliances. For example, the tourniquet body itself could be substantially of the shape and cross section taught without incorporating any reservoirs, or any means of producing exothermic reaction. For example, a pad which generates heat, whether by exothermic reaction or otherwise, could be used to temporarily overlay the entire region normally occupied by pad portion 12, including the area of window aperture 14. Upon such time as the heat from this pad had produced sufficient vasodilation of the blood vessel held within the window aperture, then the heated pad could be removed and venipuncture could then be accomplished through the window aperture identically as it is accomplished within the preferred embodiment of the invention.

Because the synergistically interactive principles expressed within the present invention are readily capable of being realized, and combined, in diverse physical embodiments, the present invention should be interpreted broadly. Particularly, the invention should be interpreted in accordance with the language of the following claims, only, and not solely in accordance with that particular preferred embodiment tourniquet in which the present invention has been taught.

What is claimed is:

1. A method for dilating at least a portion of a blood vessel prior to, and compatably with, venipuncture of the dilated blood vessel, the method comprising the steps of:
    positioning a substantially planar member having a window aperture and an extracorporeal heat source positioned therein against a body part wherein said blood vessel is located such that (i) a portion of a blood vessel is within the member's window aperture, and (ii) said extracorporeal heat source is operative to cause localized dilation of the portion of the blood vessel positioned within the window aperture; then
    inserting a needle into the dilated blood vessel portion through the member's window aperture.

2. The method according to claim 1 wherein, between the positioning and inserting steps, the method further comprises the step of:
    retaining the substantially planar member in its emplaced position against the body by securing the member with a strap extending around a portion of the body.

3. The method according to claim 2 wherein said extracorporeal heat source comprises an exothermic reaction of materials within the member.

4. The method according to claim 3 wherein the heating by exothermic reaction within the member is initiated by breaking at least one frangible barrier within the member therein allowing said materials to come into contact producing an exothermic reation.

5. The method according to claim 4 wherein the initiation of said exothermic reaction by breaking a frangible barrier results in the opening of a reservoir of liquid within the member.

6. The method according to claim 5 wherein the initiation of an exothermic reaction by breaking a frangible barrier results in allowing liquids contained within two reservoirs within the member to come into contact with each other, thereby producing the exothermic reaction.

7. The method according to claim 1 which, after the inserting step, further comprises the step of:
    opening a channel within the member between the member's window aperture and an outer edge of the substantially planar member so as to relieve any constriction of the blood vessel induced by that portion of the member, thereby facilitating drainage of blood from the dilated portion of said blood vessel.

8. The method according to claim 7 wherein the opening of a channel within the member is accomplished by ripping the plane of the member.

9. The method according to claim 8 wherein the opening of a channel by ripping comprises the step of severing the member along a preexisting tear line within the member.

10. The method according to claim 9 wherein the step of severing of the member by ripping along a tear line further comprises the pulling of a rip cord which is operative to cause said severance.

11. A device for reducing the pain normally associated with needle penetration of a patient's flesh during injection or venipuncture, the device comprising:
    a flesh contacting member having an open aperture formed therein, said member being sized and configured to be positionable against a portion of the body; and
    an extracorporeal heat source operative to thermally stimulate the skin and cause localized dilation of a portion of the blood vessel, thereby minimizing the pain of a needle penetration transpiring through said open aperture.

12. The device in accordance with claim 11 wherein the means for heating is producing heat by an exothermic reaction.

13. The device in accordance with claim 11 wherein the extracorporeal heat source comprises an exothermic reaction within the body of the member.

14. The device in accordance with claim 12 wherein the exothermic reaction is initiated by the manual breaking of a frangible barrier within the member, thereby permitting contact between material which had been separated by said frangible barrier.

15. The device in accordance with claim 12 further comprising:
   strap means for holding the member against a portion of the body.

16. A method for vasodilating a portion of a blood vessel prior to, and compatably with, venipuncture of the vasodilated blood vessel portion, the method comprising the steps of:
   warming a substantially planar member having a window aperture formed therein, said warming being accomplished by an exothermic reaction of materials within the member;
   emplacing the substantially planar warm member having a window aperture against a patient's flesh so that (i) a portion of a blood vessel is within the member's window aperture, and (ii) a heating of the blood vessel by the member's warmth is sufficient to cause localized vasodilation of the portion of the blood vessel within the member's window aperture; then
   inserting a needle into the vasodilated blood vessel portion through the member's window aperture.

17. The method according to claim 16 wherein the heating by exothermic reaction within the member is initiated by breaking at least one frangible barrier within the member therein allowing materials to come into contact producing an exothermic reaction.

18. A method for stabilizing a blood vessel during venipuncture, said method comprising the steps of:
   emplacing a substantially planar member having a window aperture against a patient's flesh; and
   securing the member in contact with the patient's flesh so that a portion of a blood vessel of the patient, which portion is subject to venipuncture, lies within the member's window aperture;
   warming the substantially planar member sufficiently to cause dilation of the blood vessel lying within the window aperture, said warming being accomplished by an exothermic reaction occurring within the member;
   inserting a needle into the portion of the blood vessel lying within the member's window aperture.

19. A device for dilating and stabilizing a blood vessel to permit the performance of venipuncture thereon, said device comprising:
   a pad member operative to exert pressure upon a portion of anatomical portion of the body, said pad member having an open aperture formed therethrough so as to permit the tip of a venipuncture needle to pass through the aperture and into said underlying body portion; and
   an extracorporeal heat generating means operative to apply heat to the underlying body portion so as to cause dilation of at least one blood vessel therewithin.

20. The device of claim 19 further comprising a strap member attached to said pad member and extendible around said body portion, said strap member being operative to increase the pressure exerted by the pad member on the body portion as the strap member is tightened therearound.

21. The device of claim 19 wherein said aperture is formed near the center of the pad member.

22. The device of claim 19 wherein said extracorporeal heat generating means is incorporated within the pad member.

23. The device of claim 19 wherein said heat generating means comprises a means for causing the occurrance of an exothermic chemical reaction.

24. The device of claim 19 wherein said heat generating means comprises a means for causing the occurrance of an exothermic reaction wherein oxygen is required for said exothermic reaction to proceed.

25. The device of claim 19 wherein said extracorporeal heat generating means comprises:
   a first reservoir containing a first reactant material;
   a second reservoir containing a second reactant material, said second reactant material being capable of reacting with said first reactant material to cause liberation of heat;
   a breakable barrier separating said first reservoir from said second reservoir such that rupture of said barrier will permit the first reactant material to come in contact with the second reactant material, thereby causing said heat to be liberated.

26. The device of claim 25 wherein one of said materials is a liquid.

27. The device of claim 25 wherein both of said materials are liquids.

28. The device of claim 19 wherein at least a portion of said pad is severable along a path extending from said aperture to an exterior edge of the pad, thereby relieving any pressure exerted by the pad upon the underlying body portion in the region of said path.

29. The device of claim 28 wherein the pad is severable along said path by way of a ripcord.

* * * * *